(12) United States Patent
Almeida

(10) Patent No.: US 11,690,929 B2
(45) Date of Patent: Jul. 4, 2023

(54) STERILIZATION MASK WITH UVC REFLECTIVE CHAMBER

(71) Applicant: World Hygienic LLC, Clearwater, FL (US)

(72) Inventor: Stephen Almeida, Clearwater, FL (US)

(*) Notice: Subject to any disclaimer, the term of this patent is extended or adjusted under 35 U.S.C. 154(b) by 0 days.

(21) Appl. No.: 17/394,539

(22) Filed: Aug. 5, 2021

(65) Prior Publication Data
US 2021/0361818 A1 Nov. 25, 2021

Related U.S. Application Data

(63) Continuation of application No. PCT/US2020/052495, filed on Sep. 24, 2020, and a continuation of application No. 16/898,679, filed on Jun. 11, 2020, now abandoned.

(60) Provisional application No. 62/985,155, filed on Mar. 4, 2020.

(51) Int. Cl.
| A61L 9/20 | (2006.01) |
| A62B 18/02 | (2006.01) |
| A62B 23/02 | (2006.01) |
| A41D 13/11 | (2006.01) |

(52) U.S. Cl.
CPC .............. *A61L 9/20* (2013.01); *A62B 18/025* (2013.01); *A62B 23/02* (2013.01); *A41D 13/1161* (2013.01); *A61L 2209/12* (2013.01); *A61L 2209/14* (2013.01)

(58) Field of Classification Search
None
See application file for complete search history.

(56) References Cited

U.S. PATENT DOCUMENTS

| 4,886,056 A | 12/1989 | Simpson |
| 5,165,395 A | 11/1992 | Ricci |
| 5,698,866 A | 12/1997 | Doiron et al. |
| 6,171,548 B1 * | 1/2001 | Rose .................. A61L 9/20 422/128 |
| 6,257,235 B1 | 7/2001 | Bowen |
| 8,252,099 B2 | 8/2012 | Worrilow |
| 8,584,676 B2 | 11/2013 | Gossweiler |
| 8,733,356 B1 | 5/2014 | Roth |
| 10,335,618 B2 * | 7/2019 | Zhou ................ A62B 18/10 |

(Continued)

FOREIGN PATENT DOCUMENTS

JP 2017530730 A * 10/2017

*Primary Examiner* — Andrew Smyth
(74) *Attorney, Agent, or Firm* — Larson & Larson; Justin P. Miller; Frank Liebenow

(57) ABSTRACT

The sterilization mask with UVC reflective chamber includes a chamber with reflective liner, through which inhaled and exhaled air passes. The reflective chamber is also referred to as a sterilization chamber. Using a reflective chamber ensures each photon of UVC light has a long life, thus dissipating slowly. Increasing the life of the UVC photons decreases the quantity of photons that must be created. Thus, less power is required to achieve the sterilization. Sterilization is defined as a 6-log reduction (99.9999%) of various microbes including viruses, bacteria, and spores. The reflective chamber is made reflective using an UVC internal reflective surface. This surface is preferably formed from ePTFE, or other equivalently UVC reflective material.

15 Claims, 15 Drawing Sheets

(56) References Cited

U.S. PATENT DOCUMENTS

| | | | |
|---|---|---|---|
| 2007/0101867 A1* | 5/2007 | Hunter | A62B 23/02 |
| | | | 96/224 |
| 2007/0163588 A1 | 7/2007 | Hebrank et al. | |
| 2009/0205664 A1 | 8/2009 | Lyon | |
| 2010/0128901 A1* | 5/2010 | Herman | H04R 1/086 |
| | | | 381/98 |
| 2012/0279503 A1 | 11/2012 | Zhou et al. | |
| 2016/0001108 A1* | 1/2016 | Zhou | A62B 7/10 |
| | | | 128/863 |
| 2016/0038624 A1* | 2/2016 | Krosney | A61L 9/20 |
| | | | 250/436 |
| 2017/0202988 A1* | 7/2017 | Clark | A61L 2/10 |
| 2018/0021471 A1* | 1/2018 | Krosney | B01D 53/007 |
| | | | 422/4 |

* cited by examiner

STERILIZATION MASK WITH UVC REFLECTIVE CHAMBER

CROSS-REFERENCE TO RELATED APPLICATION

This application claims priority to:

U.S. Patent Application 62/985,155, filed Mar. 4, 2020, titled UVC Anti-microbial mask and modules;

U.S. patent application Ser. No. 16/898,679, filed Jun. 11, 2020, titled UVC anti-microbial breathing sterilizing modules, masks, and devices; and PCT Application PCT/US20/52495, filed Sep. 24, 2020, titled UVC anti-microbial breathing sterilizing modules, masks, and devices.

FIELD

This invention relates to the field of air sterilization and more particularly to a portable device for sterilizing air.

BACKGROUND

Sanitizing air is critical to preventing the spread of airborne diseases.

The COVID-19 pandemic has highlighted the value of sterilizing both air that a user will inhale, and air a user has exhaled. By sanitizing both air streams, the user avoids infection from surrounding air, and surrounding third-parties avoid contracting airborne diseases from the user.

Ideally such a sterilizing device is portable, allowing a user to wear it in any setting, from a hospital to a grocery store.

But requiring sterilization of both incoming and outgoing air increases the power requirements for a portable unit.

What is needed is a means of increasing the efficiency of a portable air sterilization device to decrease its power requirements, thus making a portable unit practical.

SUMMARY

The sterilization mask with UVC reflective chamber includes a chamber with reflective liner, through which inhaled and exhaled air passes. The reflective chamber is also referred to as a sterilization chamber.

Using a reflective chamber ensures each photon of UVC light has a long life, thus dissipating slowly. Increasing the life of the UVC photons decreases the quantity of photons that must be created. Thus, less power is required to achieve the sterilization.

Sterilization is defined as a 6-log reduction (99.9999%) of various microbes including viruses, bacteria, and spores.

The reflective chamber is made reflective using a UVC internal reflective surface. This surface is preferably formed from ePTFE, or other equivalently UVC reflective material.

The use of ePTFE is ideal because it is 95% reflective in the frequency of UVC light. Thus, a single UVC photon can bounce twelve times before dissipating. As compared to a surface with no reflectivity, only $\frac{1}{12}$ as much UVC light is needed to accomplish the same level of UVC concentration.

Other materials, such as aluminum, have only a 70% reflectance at best, thus losing 30% of the UVC energy at each bounce.

With the UVC light providing sterilization, the remaining requirement for air cleaning is particle filtration. This is accomplished using one or more filters. For example, pre-filters for large dust particles and aerosols. Air may also be filtered through stainless-steel cup filters that remove larger particles.

While filtration is important, it creates resistance to airflow. If this resistance is too high, such that the user perceives the resistance as an inability to breathe, it may result in panic and removal of the mask.

The solution is to create positive air pressure, compensating for the resistance of the filter.

In a first embodiment, the airflow is only in one direction, thus permitting a single fan to consistently push at the inlet, or pull at the outlet. But a fan that covers the entire inlet can create problems given the sinusoidal action of breathing. A fan that runs at a consistent speed will at times provides too much air, and too little at other times. Allowing the fan to increase and decrease speed can create unwanted noise.

Thus, a mechanical solution is ideal. In particular, discharging the fan through a perforated baffle. The holes, or perforations, in the baffle allow excess air to exit the system, or additional air to be drawn in. While fan may not keep up with peak air intake, it creates positive pressure and thus counteracts the resistance of the filter and increases user comfort.

As an alternative to a fan, the device may use the flow of warm air from the heatsink to create negative pressure at the air outlet. This helps to draw air out, thus helping the user to overcome the resistance of the filters. In summary, air that is warmed by the heatsink—the heat created by the device's electronics—is passed across the exhaust, pulling air out of the device.

Returning to sterilization, to further increase the effectiveness of UVC light sterilization, sonic agitation is optionally added to prevent shadowing. Shadowing occurs when a particle in the airstream shields, or blocks, particles that are behind it, or in its shadow.

Creating a longitudinal wave within the sterilization chamber moves particles back and forth, thus shifting particles with respect to each other, thereby allowing light to access all of the airstream. The particles do not move down the tube with the wave—the wave does not create flow—rather the particles oscillate back and forth about their individual equilibrium positions.

The preferred frequency range is 1 hz to 5 Ghz.

The preferred embodiment uses a single sonic oscillator, but the use of multiple sonic oscillators is anticipated.

If using paired, opposing sonic oscillators, the sonic oscillators must pulse in the same direction to create matching action (e.g., both left, then both right, then both left).

To further reduce the UVC light quantity, and to prevent the escape of UVC light, the ends of the sterilization chamber are constructed as UVC trapping exits. Rather than escaping, any UVC light is either reflected back into the chamber or absorbed.

The action of trapping UVC light is accomplished by a mix of geometry and materials.

The geometry includes steep exit angles that prevent UVC photons from passing straight out. If photons bounce into the exit passage, they may encounter radial-angle deflectors that push photons back into the chamber.

If the photons avoid reflection, they will instead be absorbed by UVC absorbing material.

As an additional means of managing power consumption, the sterilization mask with UVC reflective chamber can adjust the UVC intensity is depending on the user's breathing intensity and/or pattern.

Since airflow varies with both inhale and exhale, a continuous flux UVC system would need to irradiate enough UVC flux to achieve a 6-log reduction at the peak airflow rate. It is inefficient to sterilize at such an intensity when the air is static, such as between breaths, or during low-flow periods as breath increases or decreases. When the device is battery-powered, the result of over-consumption is reduced battery life and excessive heat production.

Using an airflow sensor, the device detects airflow, adjusting UVC flux to achieve sterilizing but without excess power consumption. If a user's breathing rate exceeds sterilization capacity, an alarm sounds to alert the user that the air may not be fully sterilized.

As a practical matter, communicating with a mask user is difficult. Covering the nose and mouth muffles sounds, and distorts speech. Mask wearers may remove or lift their mask to speak, eliminating the benefits of wearing a mask.

Simply placing a microphone inside the mask is a poor solution, the microphone capturing reverberations and echoes, making the user difficult to understand.

To solve this problem, a thru-hole is created through the mask. A membrane is placed across the hole, the membrane able to pass vibrations without compromising the sealed nature of the mask.

The membrane material is selected to readily vibrate at the frequencies of human speech, but to dampen or absorb lower-frequency vibrations. The membrane also dampens low-amplitude vibrations. The result is that reverberations and echoes lack the strength to pass through the membrane, thus cleaning up the transmission of speech.

Following the membrane is a tube or channel of sound-absorbing foam, at the end of which is placed a sound-absorbing microphone. The microphone is preferably unidirectional to minimize sound picked up from the operation of the sterilization module.

The microphone passes a signal to an amplifier, then an equalizer, and finally to an external speaker.

In an alternative embodiment of the sterilization mask with UVC reflective chamber, the reflective chamber is divided to create unidirectional air flow. This arrangement is an alternative to a bidirectional system, where inhaled and exhaled air pass back and forth through a single chamber. Bidirectional systems have the drawback of failing to fully exhaust all exhaled air, resulting in the next inhalation being warmer and with increased carbon dioxide.

But using two UVC chambers increases the size of a device, as well as complexity. Thus, this problem is best solved by using a single UVC chamber with two airways. Valves control the flow direction of the air, keeping the flow unidirectional. The two flow paths are separated by a UVC-transparent film, allowing a single set of UVC emitters to sterilize two separate flow paths.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
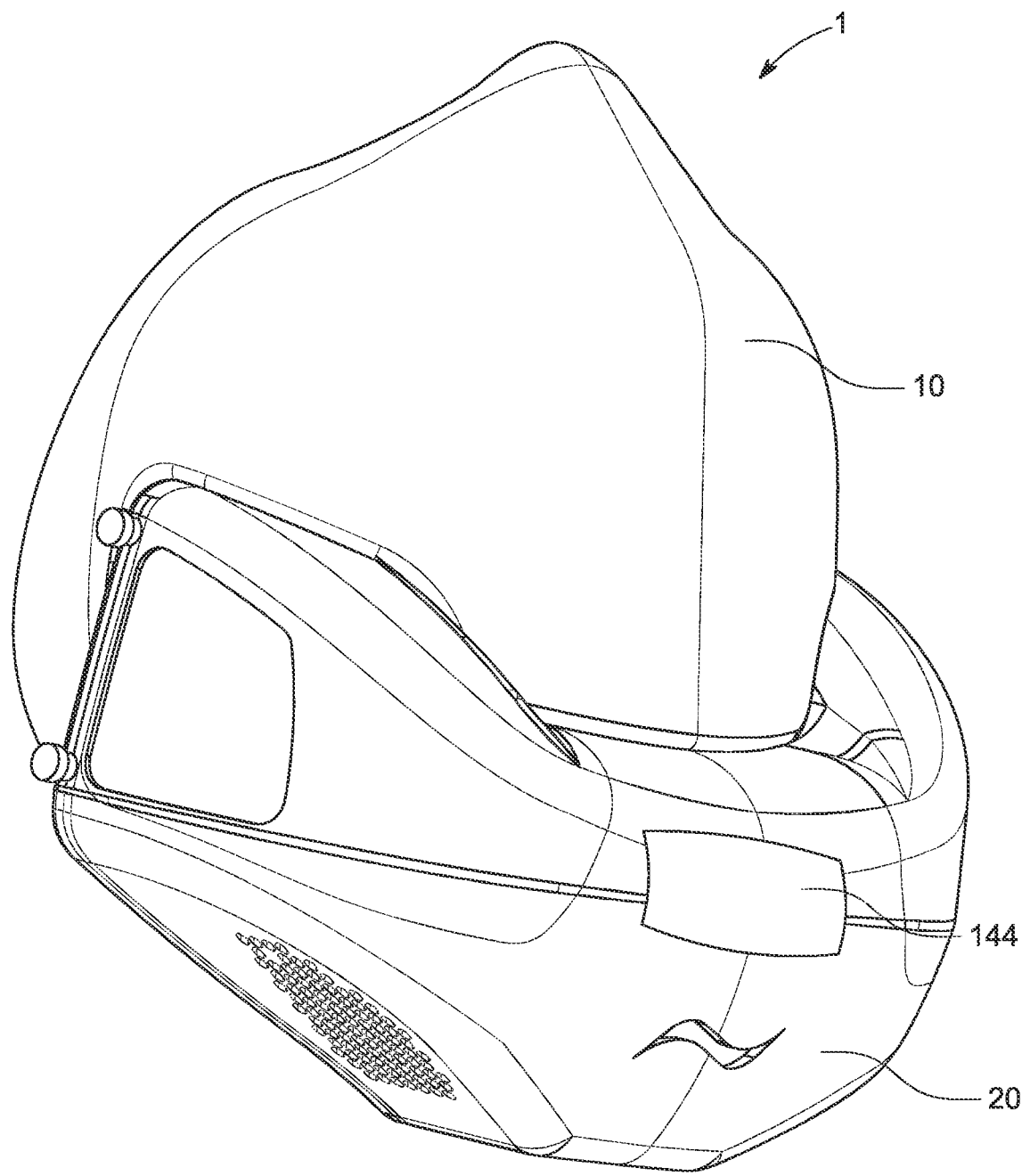
FIG. 1 illustrates a first isometric view of the sterilization mask with UVC reflective chamber.

Reference will now be made in detail to the presently preferred embodiments of the invention, examples of which are illustrated in the accompanying drawings. Throughout the following detailed description, the same reference numerals refer to the same elements in all figures.

Referring to FIG. 1, a first isometric view of the sterilization mask with UVC reflective chamber is shown.

The sterilization mask with UVC reflective chamber 1 is shown formed from primary components of the flexible mask 10 and the sterilization module 20.

Also shown is speaker 144, where the user's voice is emitted.

Figure 2:
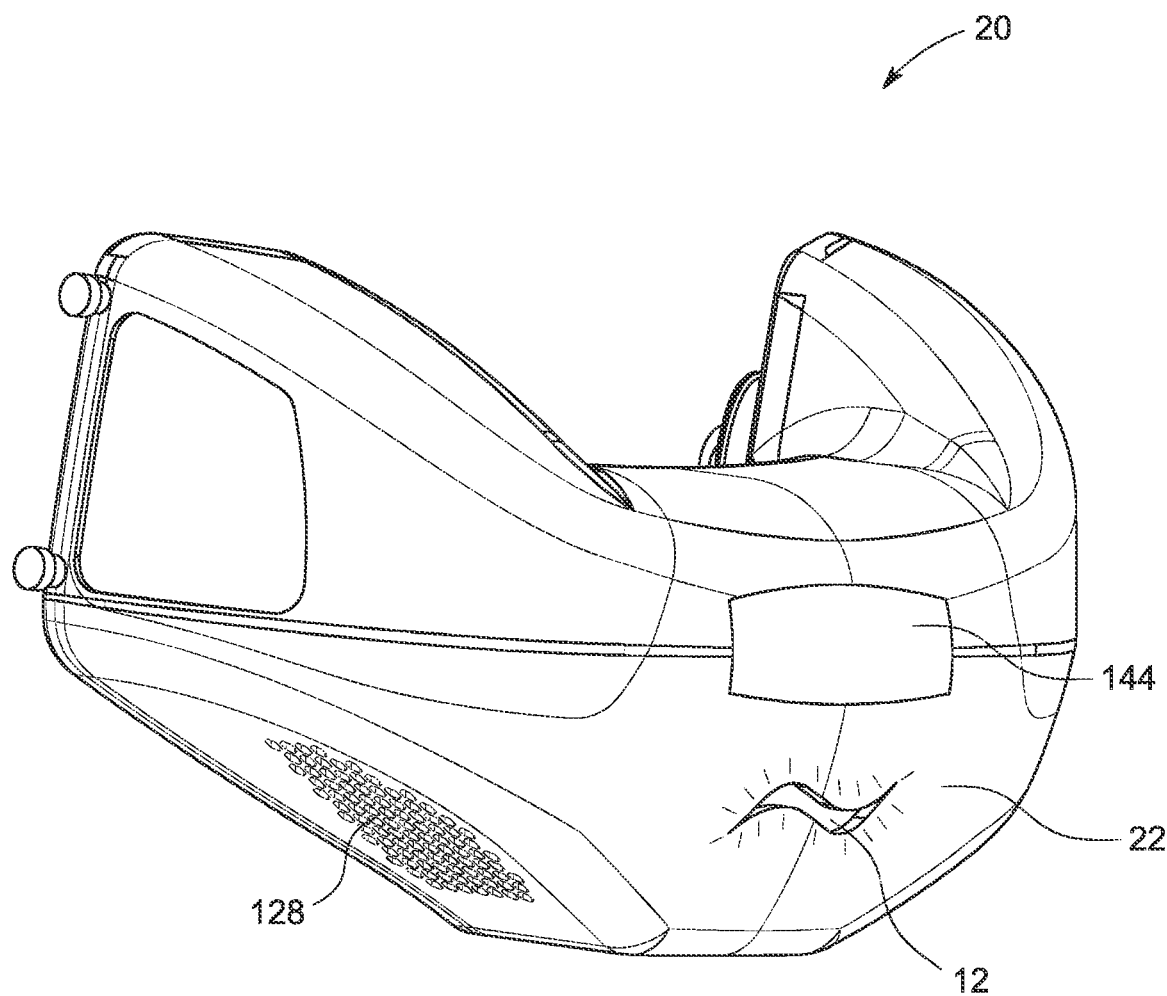
FIG. 2 illustrates a second isometric view of the sterilization module of the sterilization mask with UVC reflective chamber.

Referring to FIG. 2, a second isometric view of the sterilization module of the sterilization mask with UVC reflective chamber is shown.

The sterilization module 20 includes a housing 22 that protects the interior components.

Indicator light 12 activates to show that the sterilization mask with UVC reflective chamber 1 is operating.

Excess heat from operation is exhausted through warm air outlet 128.

Figure 3:
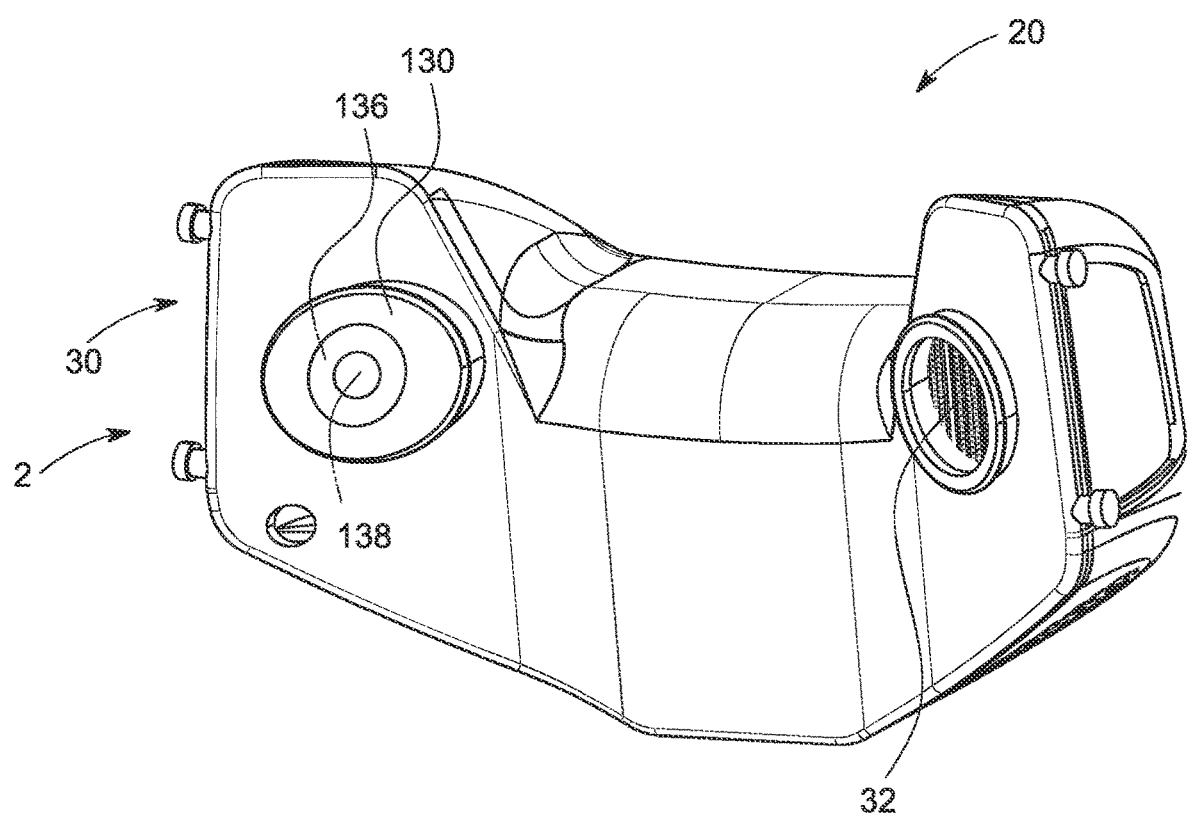
FIG. 3 illustrates a rear isometric view of the sterilization module of the sterilization mask with UVC reflective chamber.

Referring to FIG. 3, a rear isometric view of the sterilization module of the sterilization mask with UVC reflective chamber is shown.

As the user breathes in, the sterilization module 20 takes in air 2 via the atmospheric inlet/outlet 30, which is sterilized and passed to the user through the mask inlet/outlet 32. The reverse occurs as the user breathes out.

Also shown the exterior of audio components 130, including membrane 136 and hole 138.

Figure 4:
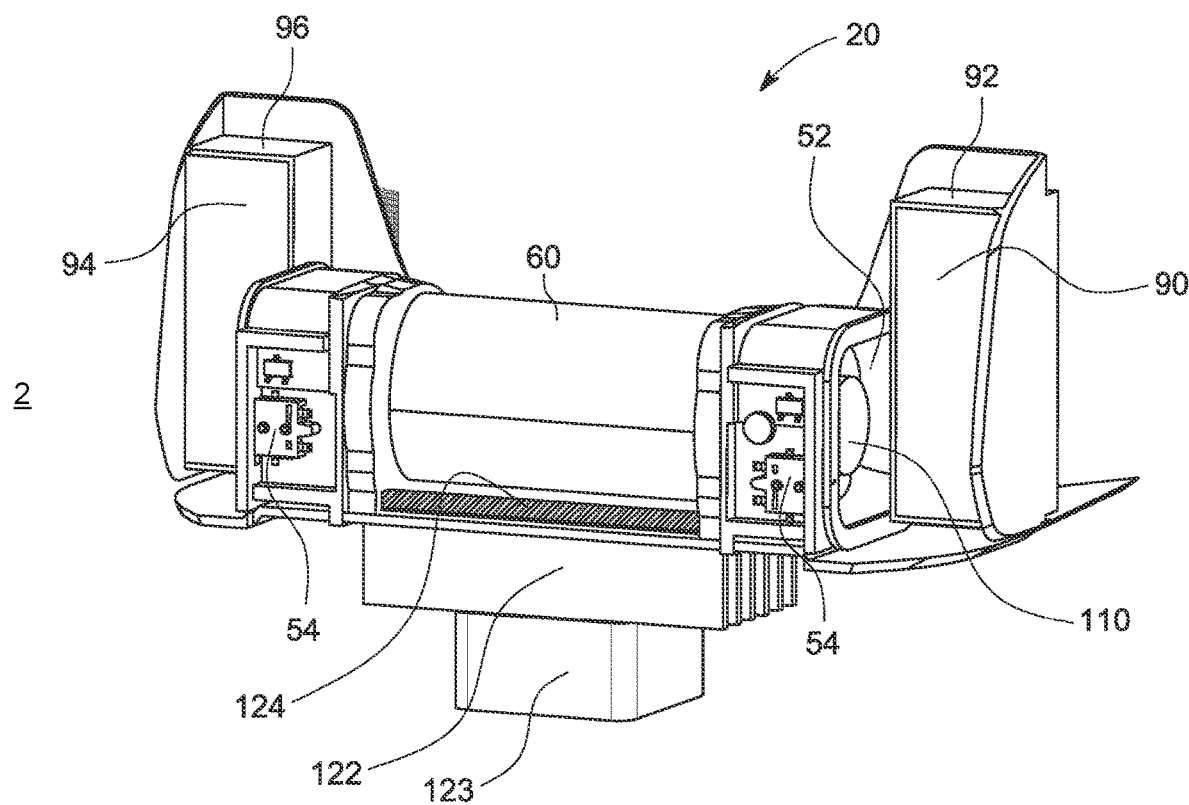
FIG. 4 illustrates an interior view of the sterilization module of the sterilization mask with UVC reflective chamber.

Referring to FIG. 4, an interior view of the sterilization module of the sterilization mask with UVC reflective chamber is shown.

The interior of the sterilization module 20 includes first filter 90 held within first filter holder 92, and second filter 94 held within second filter holder 96.

The filters 90/94 act to prefilter incoming air whether incoming from the atmosphere or from within the mask, i.e., from the user's exhalations.

Stainless steel screens 52 on each end of the reflective chamber 60 further filter the air 2. The presence of the stainless-steel screens 52 is monitored by the screen monitoring switches 54, which trigger an alarm if a screen 52 is missing.

After filtering, air 2 passes through the reflective chamber 60 wherein it is sterilized.

A heat sink 122 rests in contact with the aluminum UVC circuit board 124, drawing heat away. A heat sink fan 123 brings in outside air to cool the heat sink 122.

Figure 5:
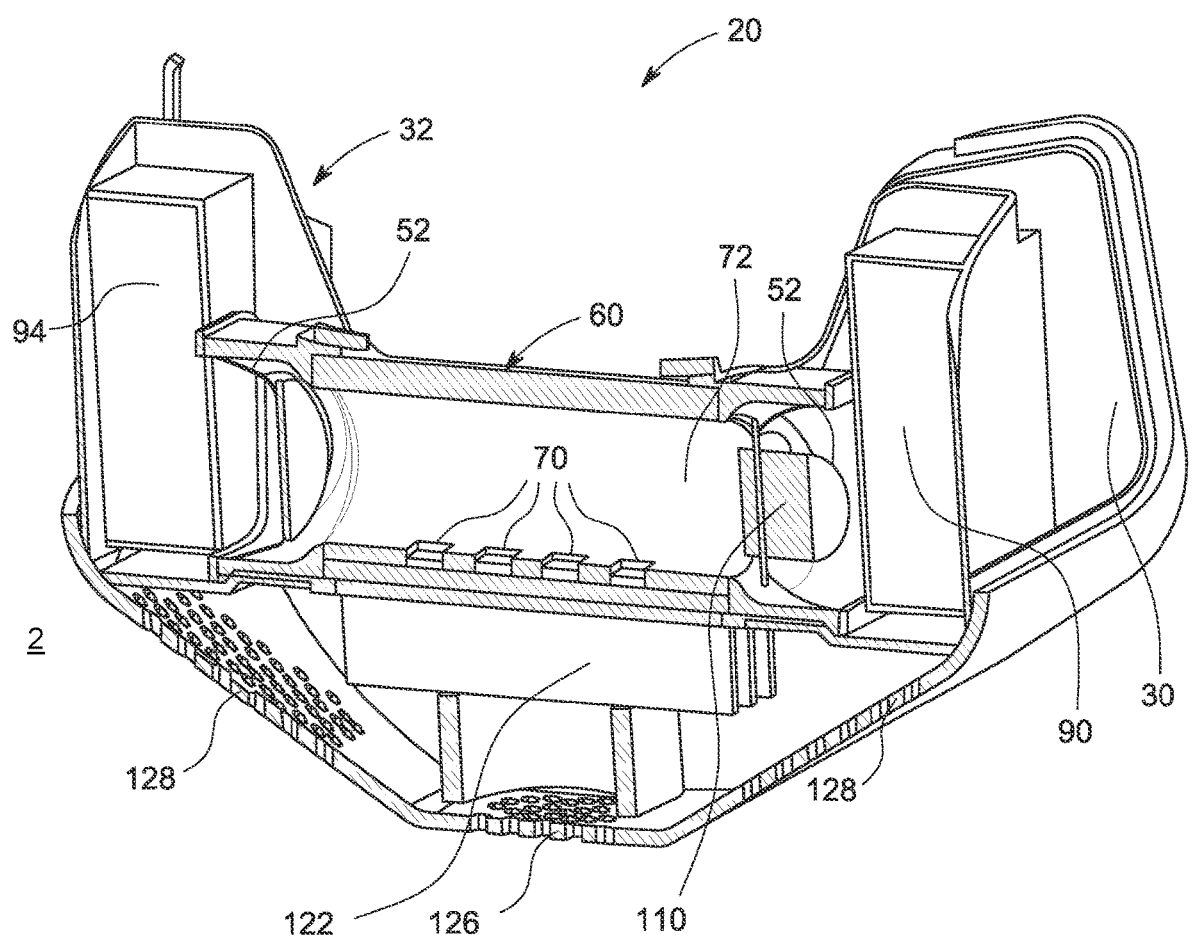
FIG. 5 illustrates a cutaway view of the rear of the sterilization module of the sterilization mask with UVC reflective chamber.
Figure 6:
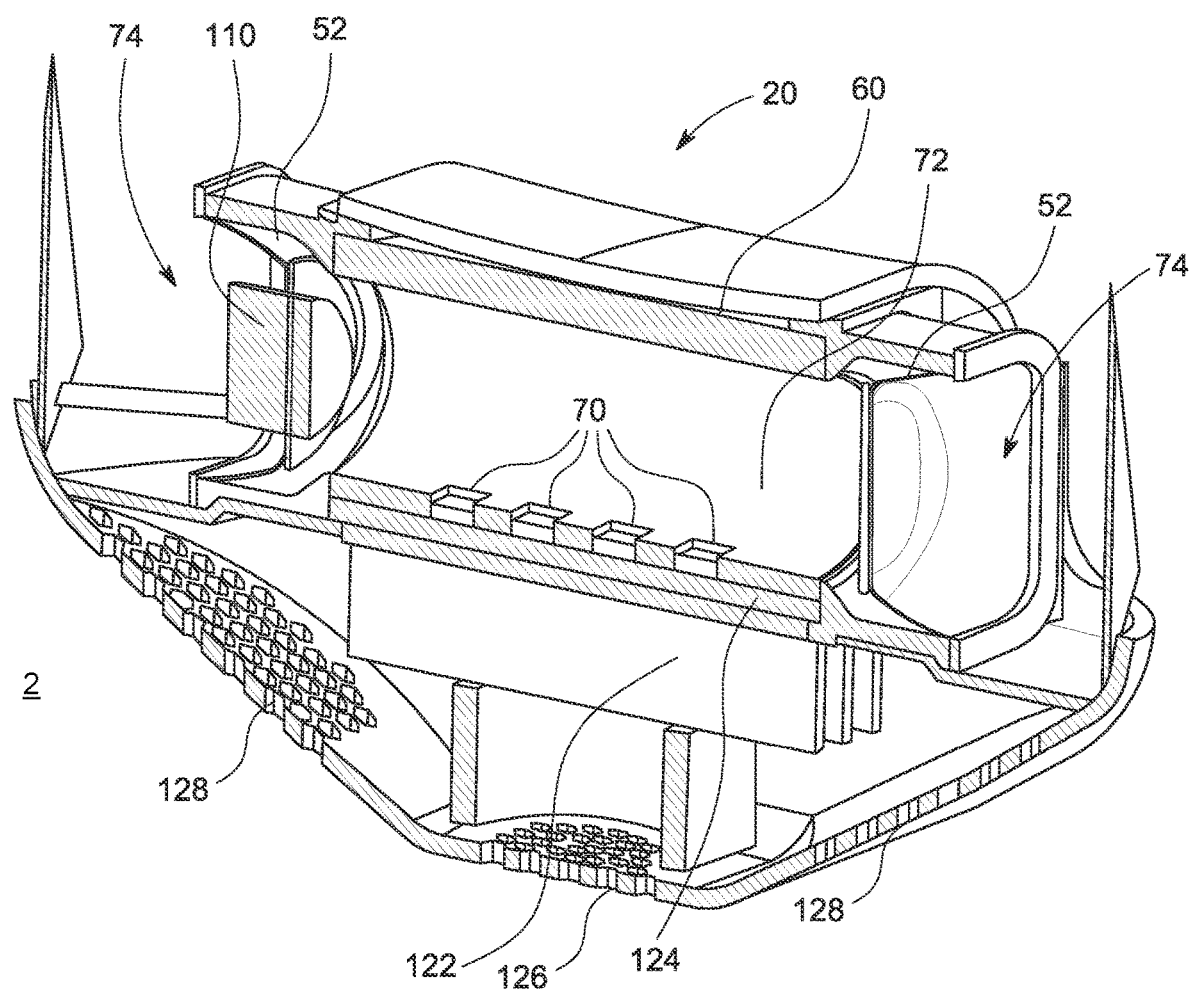
FIG. 6 illustrates a cutaway view of the front of the sterilization module of the sterilization mask with UVC reflective chamber.

Referring to FIGS. 5 and 6, cutaway views of the rear and front of the sterilization module of the sterilization mask with UVC reflective chamber are shown.

The sterilization module 20 is shown with reflective chamber 60, within which are the UVC emitters 70 that emit light against the UVC reflective interior surface 72.

The reflective chamber 60 ends in UVC trapping exits 74 that prevent the escape of UVC light.

A stainless-steel screen 52 sits at each end of the reflective chamber 60, filtering any air 2 entering the reflective chamber 60.

Also shown are the heat sink 122, cooled by air 2 passing into the cooling air inlet 126, and out the warm air outlet 128.

Figure 7:
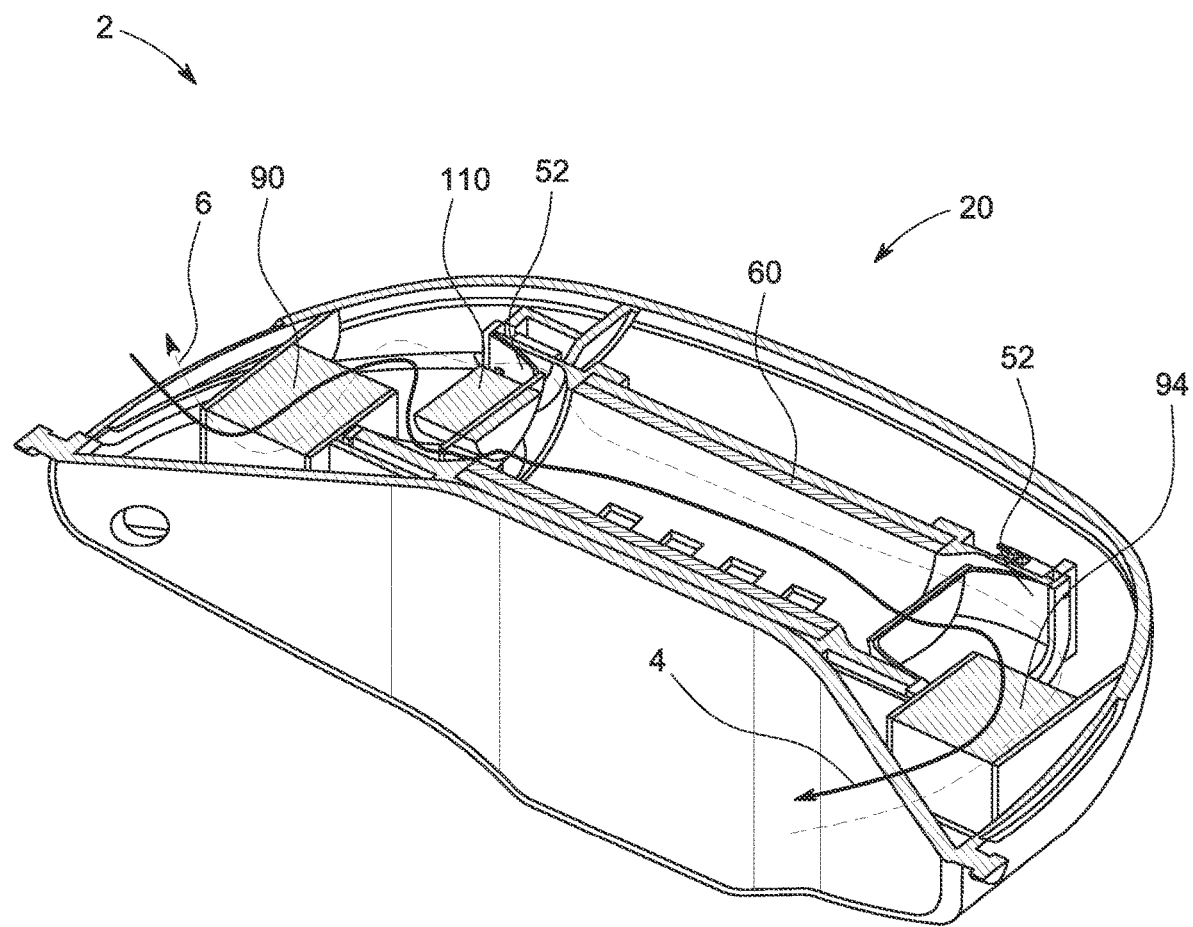
FIG. 7 illustrates a lower cutaway view of the sterilization module of the sterilization mask with UVC reflective chamber.
Figure 8:
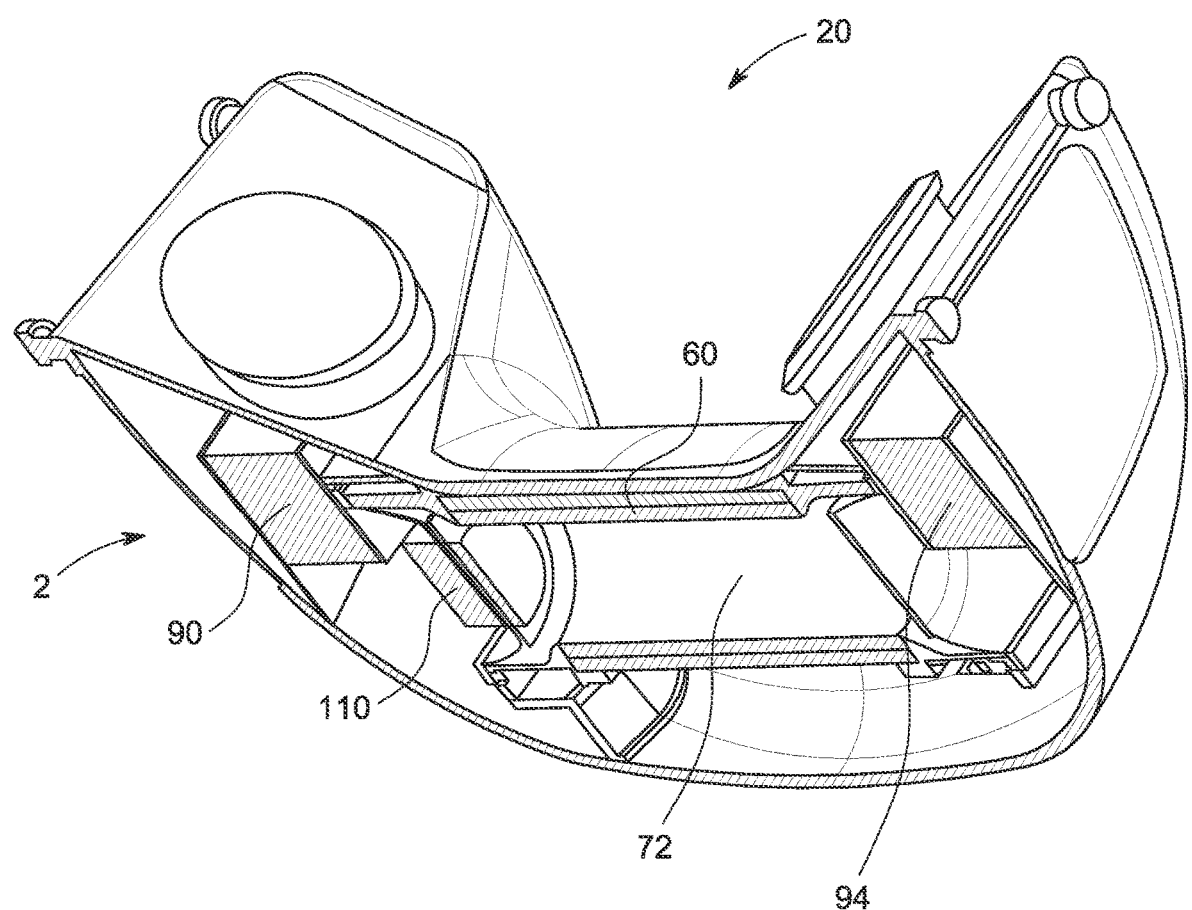
FIG. 8 illustrates an upper cutaway view of the sterilization module of the sterilization mask with UVC reflective chamber.

Referring to FIGS. 7 and 8, a lower cutaway view and an upper cutaway view of the sterilization module of the sterilization mask with UVC reflective chamber are shown.

Air 2 follows the inhalation flow 4 during a user's inhalation, and exhalation flow 6 during an exhalation.

Both flows 4/6 pass through the first filter 90, stainless steel screen 52, reflective chamber 60, stainless steel screen 52, and second filter 94, passing through the elements in opposing directions.

The sonic agitator 110 is also visible, placed at one end of the reflective chamber 60. Alternative placement of the sonic agitator 110 is anticipated, so long as it may still move the air within the reflective chamber 60.

Figure 9:
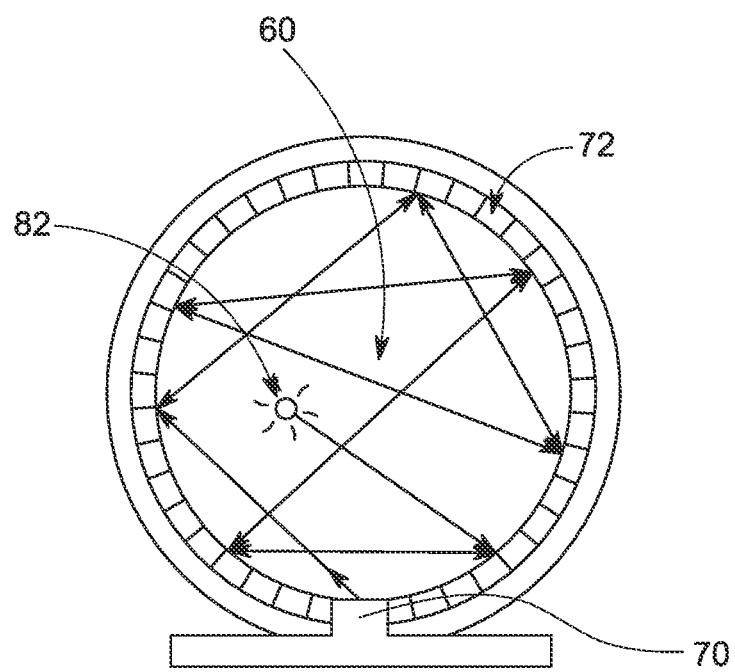
FIG. 9 illustrates a schematic view of the reflective chamber, in cross-section, of the sterilization mask with UVC reflective chamber.

Referring to FIG. 9, a schematic view of the reflective chamber, in cross-section, of the sterilization mask with UVC reflective chamber is shown.

The reflective chamber 60 includes one or more UVC emitters 70 that emit photons 82.

The photons 82 bounce inside the reflective chamber 60, reflected by the UVC reflective interior surface 72. The result of the highly-reflective UVC reflective interior surface 72 is that the photons 82 have a long life, and thus can sterilize larger volumes of air, thus lowering power consumption of the UVC emitters 70.

Figure 10:
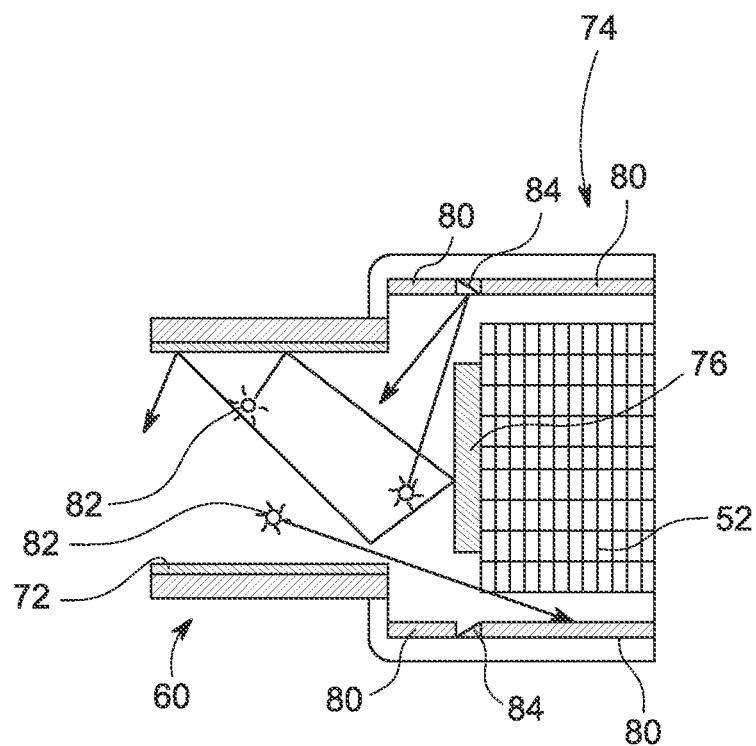
FIG. 10 illustrates a schematic view of an end, or UVC absorbing chamber, of the reflective chamber, of the sterilization mask with UVC reflective chamber.

Referring to FIG. 10, a schematic view of an end of the reflective chamber, of the sterilization mask with UVC reflective chamber is shown.

The UVC trapping exit 74 is shown with multiple features to prevent the escape of photons 82.

As photons 82 bounce around the reflective chamber 60, reflected by the UVC reflective interior surface 72, they reach the UVC trapping exit 74.

The centrally-mounted stainless steel screen 52 leaves space around the perimeter for air to exit. By only allowing a perimeter exit, the photons 82 must have a high angle to exit, making reflecting and absorbing an easier task than with an open-ended chamber.

Photons 82 may contact the UVC reflective exit surface 76, bouncing back into the reflective chamber 60.

Or photons 82 may contact the UVC exit reflector 84, which is set at angle to bounce the photons 82 back into the reflective chamber 60.

If photons 82 make it past the reflective features, they contact the UVC absorbent material 80 that consumes UVC light, preventing an exit.

Figure 11:
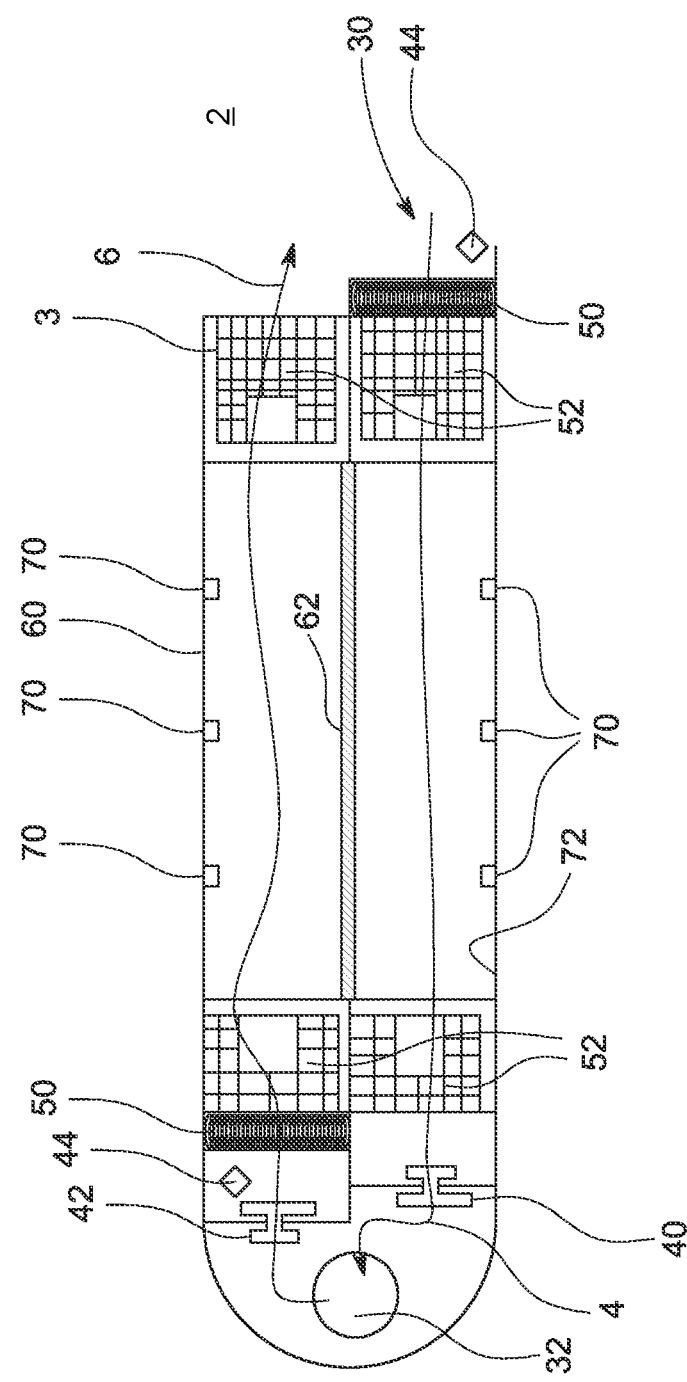
FIG. 11 illustrates a schematic view of a second embodiment of the reflective chamber, of the sterilization mask with UVC reflective chamber.

Referring to FIG. 11, a schematic view of a second embodiment of the reflective chamber, of the sterilization mask with UVC reflective chamber is shown.

The second embodiment includes two parallel flow paths for air through a single reflective chamber 60. This permits separate sterilization of incoming and outgoing air, without the requirement of two separate chambers.

Rather, a single chamber dividing wall 62 is placed across the reflective chamber 60, creating inhalation flow 4 and exhalation flow 6.

Air 2 enters from the atmosphere at the atmospheric inlet/outlet 30, entering the mask at the mask inlet/outlet 32, and then returning, but through the second half of the reflective chamber 60.

The inhalation valve 40 and exhalation valve 42 close during inhalation and exhalation respectively, ensuring air flows in the correct direction.

Incoming air passes through a prefilter element 50 to catch any particulates.

The flow meters 44 monitor inhalation flow 4 and exhalation flow 6, the volume of flow determining the intensity of the UVC emitters 70.

Also shown are the UVC emitters 70, UVC reflective interior surface 72, and stainless-steel screens 52.

Figure 12:
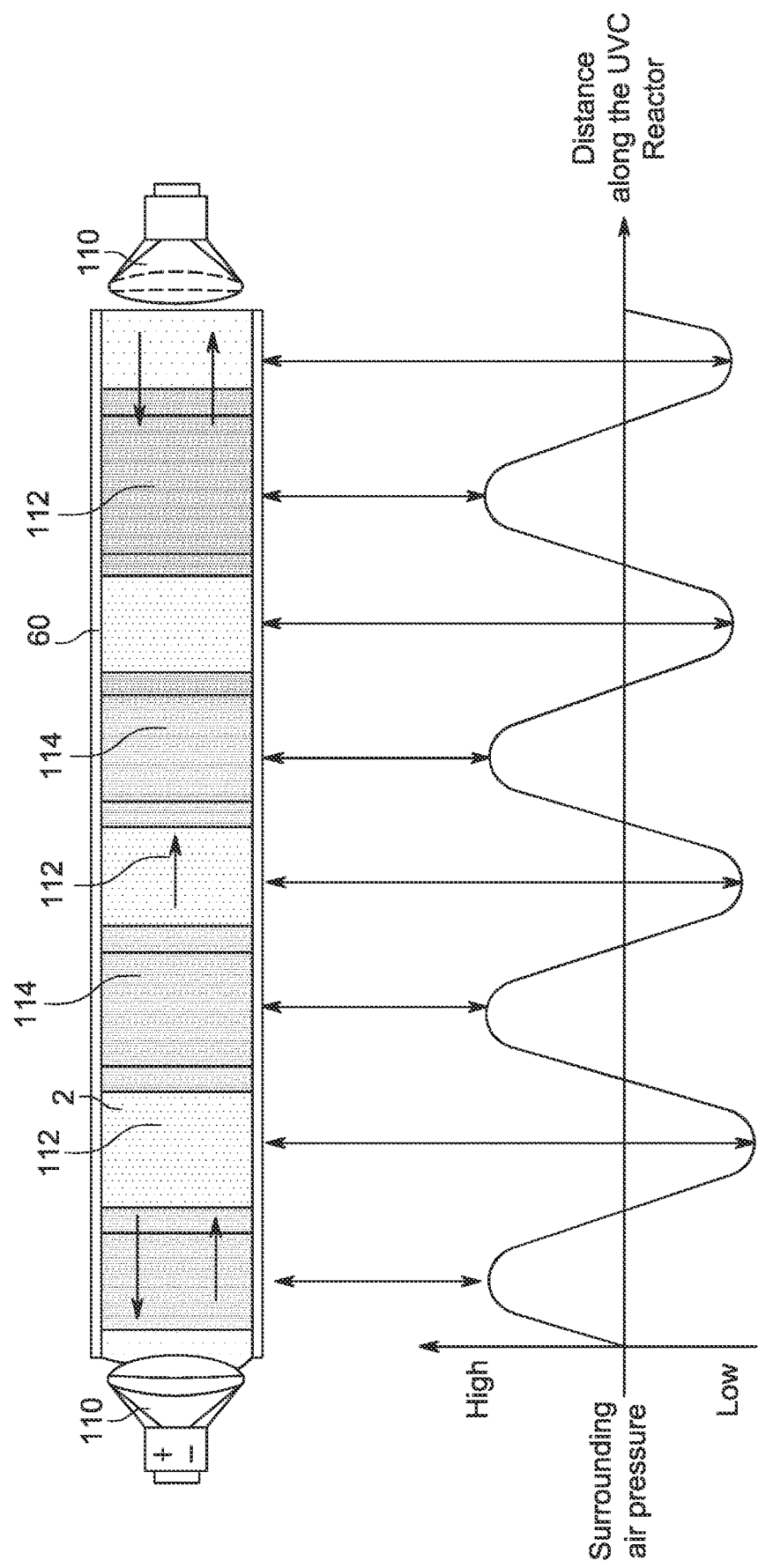
FIG. 12 illustrates a schematic view of the sonic agitator of the sterilization mask with UVC reflective chamber.

Referring to FIG. 12, a schematic view of the sonic agitator of the sterilization mask with UVC reflective chamber is shown.

The one or more sonic agitators 110 sit at one or both ends of the reflective chamber 60. The sonic agitators 110 move the air 2 via a longitudinally-moving low-pressure zones 112 and high-pressure zones 114, causing any particles in the air 2 to move back and forth. The result is that a particle that may shadow a particle behind itself is moved to the side, thus allowing UVC light to reach the shadowed particle. The result is increased effectiveness of the sterilization, again reducing power requirements.

Figure 13:
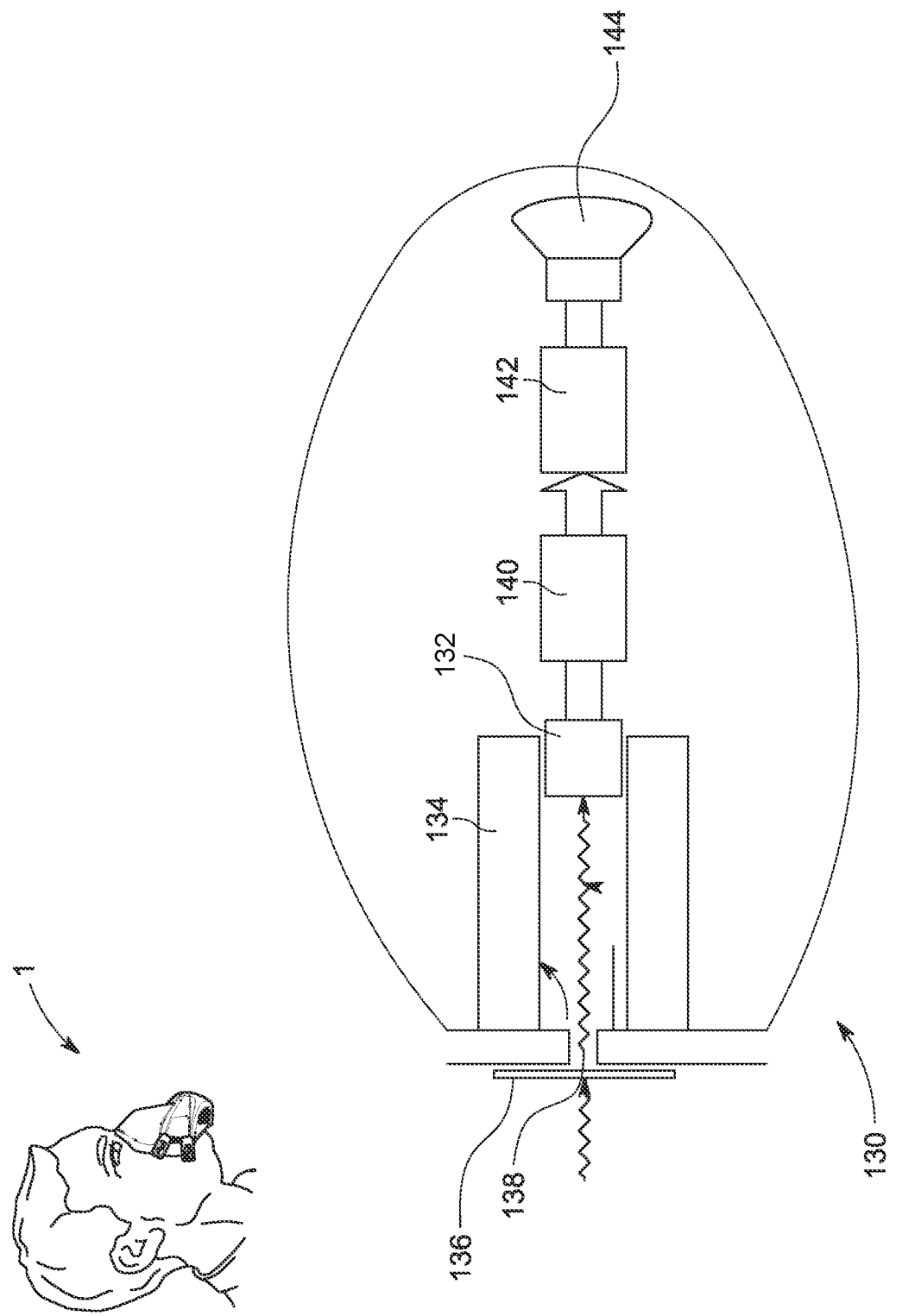
FIG. 13 illustrates a schematic view of the audio system of the sterilization mask with UVC reflective chamber.

Referring to FIG. 13, a schematic view of the audio system of the sterilization mask with UVC reflective chamber is shown.

The sterilization mask with UVC reflective chamber 1 optionally includes audio components 130 to allow the user to more readily communicate while their mouth is covered.

Sound from a user vibrates a membrane 136, placed across a hole 138. Only high-amplitude vibrations are passed through the membrane 136, eliminating echoes. Errant soundwaves are absorbed by a microphone foam surround 134. The sound then reaches the microphone 132, after which it is passed to an amplifier 140, equalizer 142, and finally to a speaker 144. The speaker 144 directs sound toward the outside of the sterilization mask with UVC reflective chamber 1, toward third-parties.

Figure 14:
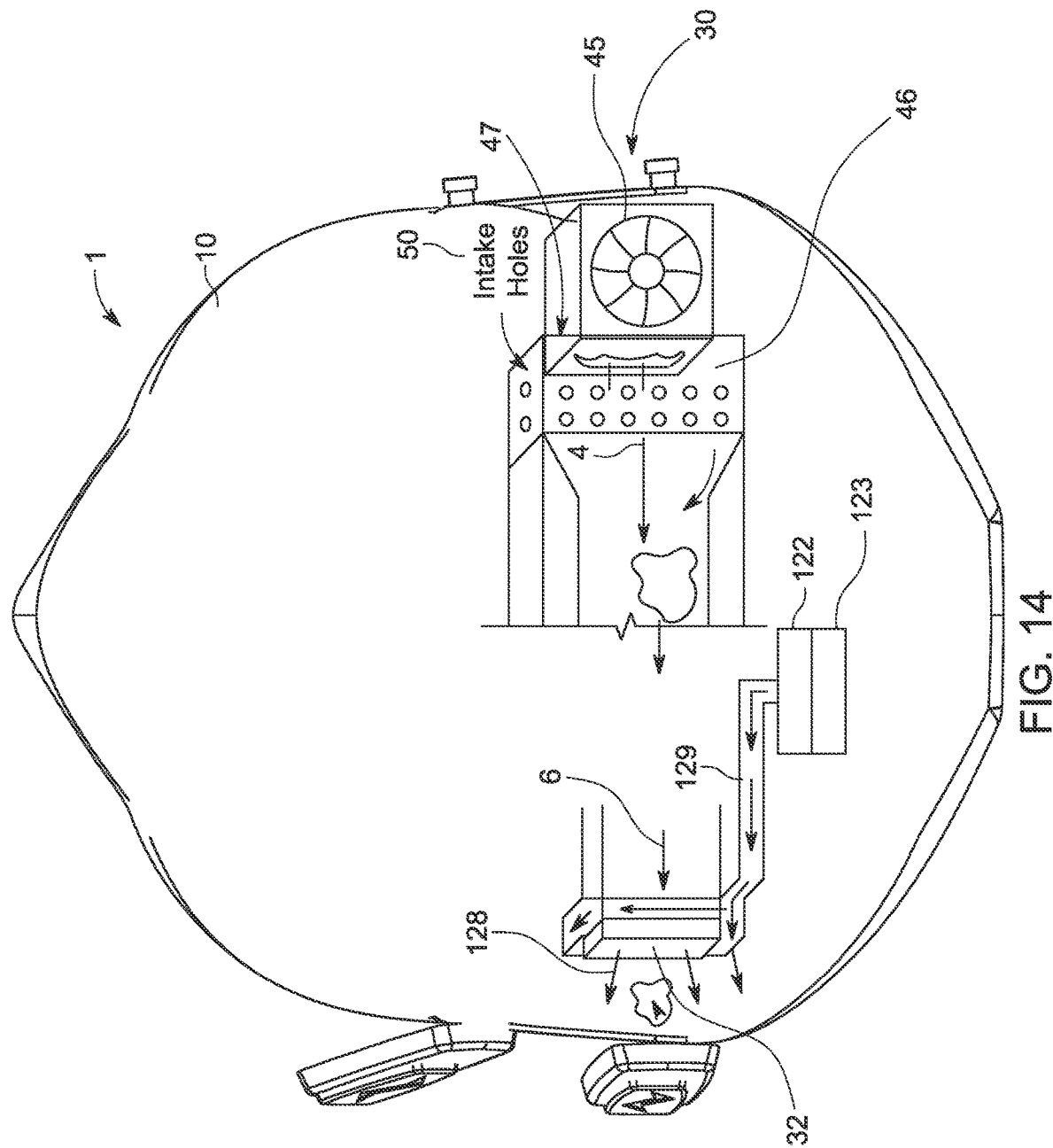
FIG. 14 illustrates a schematic view of the positive-pressure generator and waste heat pressure generation system of the sterilization mask with UVC reflective chamber.

Referring to FIG. 14, a schematic view of the waste heat pressure generation system of the sterilization mask with UVC reflective chamber is shown.

The sterilization mask with UVC reflective chamber 1 is shown with flexible mask 10.

With respect to inhalation assistance, an inhalation assist fan 45 is placed at the atmospheric inlet 30, the inhalation assist fan 45 exhausting through a perforated baffle 46. The inhalation assist fan 45 only partially covers the holes of the perforated baffle 46, creating a flow-by pathway 47 around the inhalation assist fan. The result is that if the user's inhalation demands more air than the inhalation assist fan 45 can provide, additional air 2 can bypass the fan. Thus, a fan that is smaller than the maximum inhalation flow may be used, reducing fan size and cost.

With respect to exhalation assistance, in this embodiment the heat from the heat sink 122 and heat sink fan 123 are used to create a warm air flow 129 that passes to a warm air outlet 128 placed near the mask outlet 32.

The warm air flow 129 creates a low-pressure vacuum, helping to draw exhalation flow 6 outward, lowering the effort required for breathing.

Figure 15:
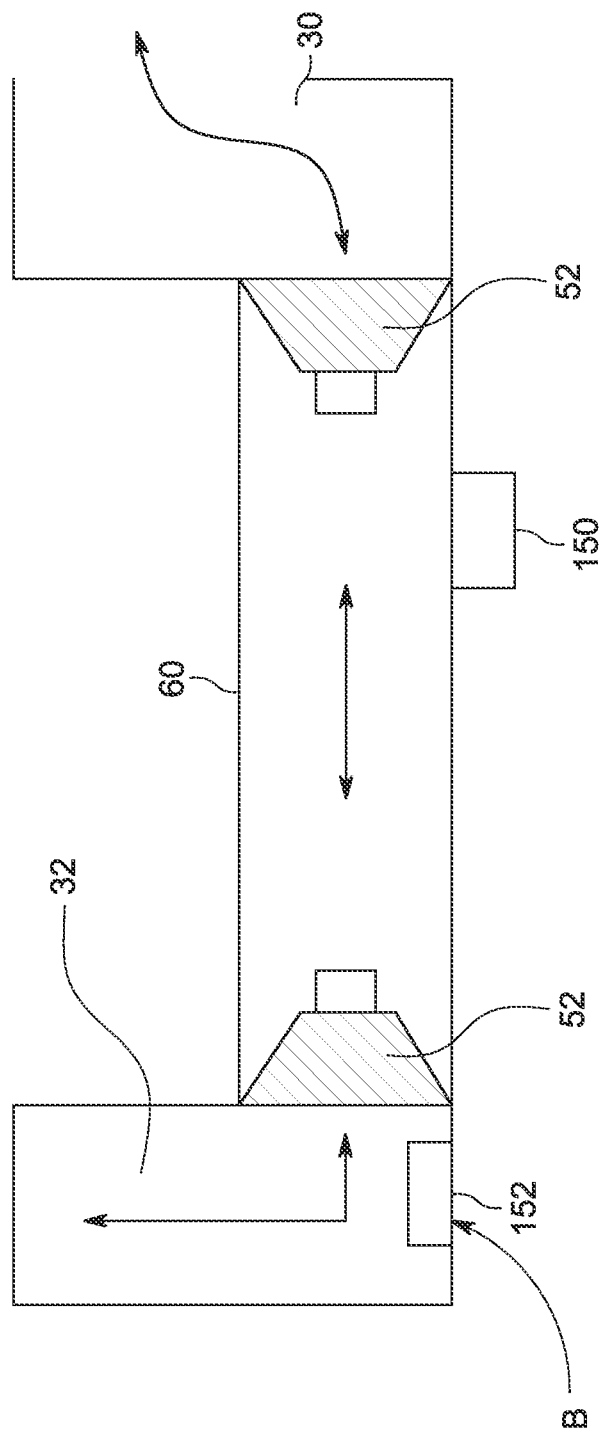
FIG. 15 illustrates a schematic view of the pressure switch system of the sterilization mask with UVC reflective chamber.

Referring to FIG. 15, a schematic view of the pressure switch system of the sterilization mask with UVC reflective chamber is shown.

The pressure switch system monitors pressure to extrapolate flow, and thus manage UVC intensity.

A first air pressure sensor 150 measures atmospheric pressure, and a second air pressure sensor 152 monitors pressure within the sterilization module 20, but outside of the reflective chamber 60. As the pressure of the second air pressure sensor 152 rises above, and falls below, the steady atmospheric pressure measured by the first air pressure sensor 150, the system can extrapolate whether the user is breathing in, breathing out, or pausing between breaths. The system can then adjust UVC intensity based on this data.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A portable air sterilization device for a user, the device passing inhaled air and exhaled air through a sterilization chamber, the device comprising:
   a chamber;
   the chamber including a mask connection point and an atmospheric connection point;
   the inhaled air and the exhaled air passing in and out of the chamber via the mask connection point;
   atmospheric air passing in and out of the chamber via the atmospheric connection point;
   a chamber dividing wall that separates the chamber into a single-direction inhalation flow path and a single-direction exhalation flow path;
   a UVC reflective interior surface lining an inside of the chamber; the UVC reflective interior surface having reflectivity of 90% or more with respect to UVC light;
   one or more UVC light sources creating UVC light within the chamber; the UVC light bouncing around the inside of the chamber by reflecting off the UVC reflective interior surface, thereby sterilizing the inhaled air and the exhaled air;
   whereby the portable air sterilization device is able to efficiently sterilize air by maximizing the life of the UVC light.

2. The portable air sterilization device of claim 1, wherein the UVC reflective interior surface is expanded polytetrafluoroethylene ("ePTFE").

3. The portable air sterilization device of claim 1, further comprising:
   a UVC trapping exit that includes:
      a UVC reflective exit surface oriented perpendicular to a longitudinal axis of the chamber;
      one or more UVC exit reflectors;
         the one or more UVC exit reflectors angled with respect to the chamber, thus acting to reflect UVC light back into the chamber;
      a UVC-absorbing material within the UVC trapping exit, the UVC-absorbing material absorbing UVC light that bypasses the UVC reflective exit surface;
   whereby the UVC trapping exit prevents escape of UVC light outside of the chamber.

4. The portable air sterilization device of claim 1, further comprising:
   a sonic agitator;
      the sonic agitator placed at one end of the chamber;
      the sonic agitator vibrating to create a longitudinal wave within inhaled air and exhaled air inside of the chamber;
   whereby the longitudinal wave moves particles within the inhaled air and exhaled air to increase effectiveness of UVC light for sterilization.

5. The portable air sterilization device of claim 4, further comprising:
   a UVC trapping exit that includes:
      a UVC reflective exit surface oriented perpendicular to a longitudinal axis of the chamber;
      one or more UVC exit reflectors;
         the one or more UVC exit reflectors angled with respect to the chamber, thus acting to reflect UVC light back into the chamber;
      a UVC-absorbing material within the UVC trapping exit, the UVC-absorbing material absorbing UVC light that bypasses the UVC reflective exit surface;
   whereby the UVC trapping exit prevents escape of UVC light outside of the chamber.

6. The portable air sterilization device of claim 1, further comprising:
   a through-mask audio communication system that includes:
      a microphone placed within a foam surround;
      a membrane that separates the inhaled and exhaled air from the microphone, sound passing through the membrane;
         the membrane placed across a hole;
      a speaker to carry sound to third-parties;
   whereby the user can speak, the sound carried through the membrane, to the microphone, processed, and then output through the speaker, allowing the user to communicate with third-parties.

7. The portable air sterilization device of claim 1, wherein:
   the chamber dividing wall is transparent to UVC light, thus allowing the one or more UVC light sources to sanitize both the inhaled air and the exhaled air;
   whereby a single chamber can sterilize two flow paths without requiring additional UVC light sources.

8. A portable, wearable, UVC sterilizing mask comprising:

a sterilization chamber;
  the sterilization chamber including an inner wall;
    the inner wall separating the sterilization chamber into a single-direction inhalation flow path and a single-direction exhalation flow path;
an inhalation assistance fan;
  the inhalation assistance fan placed at an inlet to the single-direction inhalation flow path;
  the inhalation assistance fan operating during both inhalation and exhalation;
a UVC reflective material applied to the inner wall, the UVC reflective material having reflectivity of 90% or more with respect to UVC light;
one or more UVC emitters radiating UVC light into the sterilization chamber;
  the UVC light reflective off the UVC reflective material, thereby increasing a dwell time of the UVC light within the sterilization chamber;
the one or more UVC emitters having an intensity;
  the intensity automatically adjusted based on an airflow through the sterilization chamber, with increased airflow increasing intensity, and decreased airflow decreasing intensity;
whereby the portable, wearable, UVC sterilizing mask minimizes power use while sterilizing both incoming and outgoing air.

9. The portable, wearable, UVC sterilizing mask of claim 8, wherein the UVC reflective material is expanded polytetrafluoroethylene ("ePTFE").

10. The portable, wearable, UVC sterilizing mask of claim 8, further comprising:
  a UVC trapping exit that includes:
    a UVC reflective exit surface oriented perpendicular to a longitudinal axis of the sterilization chamber;
    one or more UVC exit reflectors;
      the one or more UVC exit reflectors angled with respect to the sterilization chamber, thus acting to reflect UVC light back into the chamber;
    a UVC-absorbing material within the UVC trapping exit, the UVC-absorbing material absorbing UVC light that bypasses the UVC reflective exit surface;
  whereby the UVC trapping exit prevents escape of UVC light outside of the sterilization chamber.

11. The portable, wearable, UVC sterilizing mask of claim 8, further comprising:
  a sonic agitator;
    the sonic agitator placed at one end of the sterilization chamber;
    the sonic agitator vibrating to create a longitudinal wave within inhaled air and exhaled air inside of the sterilization chamber;
    whereby the longitudinal wave moves particles within the inhaled air and exhaled air to increase effectiveness of UVC light for sterilization.

12. The portable, wearable, UVC sterilizing mask of claim 11, further comprising:
  a UVC trapping exit that includes:
    a UVC reflective exit surface oriented perpendicular to a longitudinal axis of the sterilization chamber;
    one or more UVC exit reflectors;
      the one or more UVC exit reflectors angled with respect to the sterilization chamber, thus acting to reflect UVC light back into the sterilization chamber;
    a UVC-absorbing material within the UVC trapping exit, the UVC-absorbing material absorbing UVC light that bypasses the UVC reflective exit surface;
  whereby the UVC trapping exit prevents escape of UVC light outside of the sterilization chamber.

13. The portable, wearable, UVC sterilizing mask of claim 8, further comprising:
  a through-mask audio communication system that includes:
    a microphone placed within a foam surround;
    a membrane that separates inhaled and exhaled air from the microphone, sound passing through the membrane;
      the membrane placed across a hole;
    a speaker to carry sound to third-parties;
  whereby a user can speak, the sound carried through the membrane, to the microphone, processed, and then output through the speaker, allowing the user to communicate with third-parties.

14. The portable, wearable, UVC sterilizing mask of claim 8, wherein:
  the inner wall is transparent to UVC light, thus allowing the one or more UVC emitters to sanitize both inhaled air and exhaled air;
  whereby a single chamber can sterilize two flow paths without requiring additional UVC light sources.

15. The portable air sterilization device of claim 1, further comprising:
  an inhalation assistance fan;
    the inhalation assistance fan placed at an inlet to the single-direction inhalation flow path;
    the inhalation assistance fan operating during both inhalation and exhalation;
  whereby the inhalation assistance fan provides continuous positive pressure to aid in inhalation.

* * * * *